US008420848B2

(12) United States Patent
Kulkarni

(10) Patent No.: US 8,420,848 B2
(45) Date of Patent: Apr. 16, 2013

(54) PROCESS FOR THE SYNTHESIS OF BETA GLYCEROL PHOSPHATE

(75) Inventor: Yashwant Kulkarni, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 0 days.

(21) Appl. No.: 13/142,552

(22) PCT Filed: Jan. 8, 2010

(86) PCT No.: PCT/US2010/020456
§ 371 (c)(1),
(2), (4) Date: Oct. 17, 2011

(87) PCT Pub. No.: WO2010/080969
PCT Pub. Date: Jul. 15, 2010

(65) Prior Publication Data
US 2012/0041222 A1    Feb. 16, 2012

Related U.S. Application Data

(60) Provisional application No. 61/143,566, filed on Jan. 9, 2009.

(51) Int. Cl.
*C07F 9/11*        (2006.01)
(52) U.S. Cl.
USPC .......................................................... 558/90
(58) Field of Classification Search .................. 558/90
See application file for complete search history.

(56) References Cited

U.S. PATENT DOCUMENTS

| | | |
|---|---|---|
| 3,264,378 A | 8/1966 | Dailey et al. |
| 4,463,095 A | 7/1984 | Emi et al. |
| 4,916,249 A | 4/1990 | Brachwitz et al. |
| 6,872,712 B1 | 3/2005 | Shinitzky |
| 6,914,056 B1 | 7/2005 | Shinitzky |
| 2005/0050594 A1 | 3/2005 | Rodaway et al. |

FOREIGN PATENT DOCUMENTS

| | | |
|---|---|---|
| RO | 114618 B | 10/1998 |
| WO | 2010/080969 A1 | 7/2010 |

OTHER PUBLICATIONS

International Search Report for PCT/US 10/20456, dated Mar. 12, 2010, 2 pages.
Extended European Search Report dated Aug. 2, 2012 from related European Patent Application No. 10729547.9; 6 pages.
Haftendorn, R. et al., "Synthesis of 2-Modified 1,3-Diacylglycerols," Tetrahedron, 1995, pp. 1177-1186, vol. 51, No. 4.
Karrer, P. et al., "Ueber die Glycerin-phosphorsaeuren IV," Helvetica Chimica Acta, Verlag Helvetica Chimica Acta, 1927, pp. 87-91, vol. 10, Basel, Switzerland.
Khromova, N. et al., "Preparative Synthesis of 1,2- and 1,3-Disubstituted Phosphatidic Acids," Russian Journal of Bioogranic Chemistry, 1999, pp. 268-272, vol. 25, No. 4.
Mahmoodi, N., "Synthesis of Competitive Inhibitors of Phospholipase A2 (PLA2)," Phosphorus, Sulfur and Silicon, Jan. 1, 2002, pp. 2887-2893, vol. 177, No. 12.
Pradines, A. et al., "Enzymatic Synthesis of Phosphoric Monoesters With Alkaline Phosphatase in Reverse Hydrolysis Conditions," Tetrahedron, 1988, pp. 6373-6386, vol. 44, No. 20.
Ravily, V. et al., "Synthesis of Highly Fluorinated Di-O-alk(en)yl-glycerophospholipids and Evaluation of Their Biological Tolerance," Helvetica Chimica Acta, Mar. 20, 1996, pp. 405-425, vol. 79, No. 2.
Written Opinion dated Mar. 12, 2010 from related International Patent Application No. PCT/US2010/020456; 3 pages.

*Primary Examiner* — Kristin Bianchi
(74) *Attorney, Agent, or Firm* — Polsinelli Shughart PC

(57) ABSTRACT

The present invention provides methods for the preparation of beta glycerol phosphate and its salts. In particular, the invention provides efficient methods for the synthesis of beta glycerol phosphate of high purity.

61 Claims, No Drawings

PROCESS FOR THE SYNTHESIS OF BETA GLYCEROL PHOSPHATE

FIELD OF THE INVENTION

The present invention generally relates to a method for the synthesis of beta glycerol phosphate and salts thereof (such as, e.g., glycerol 2-phosphate disodium salt hydrate). In particular, the process provides a method for the synthesis of highly pure beta glycerol phosphate, with little contamination by the alpha isomer of the product.

BACKGROUND OF THE INVENTION

The chemical glycerol phosphate (also termed glycerophosphate) has a variety of physiological and therapeutic roles, which makes it valuable to the pharmaceutical industry. In fact, it is estimated that consumer demand for glycerophosphate, specifically glycerol 2-phosphate disodium salt hydrate (BGP) is expected to triple between the years of 2007 and 2010, and currently the demand exceeds the industrial ability to supply the product.

Prior art methods of producing BGP are not capable of meeting the high demand for this product, largely due to the fact that the product typically forms as a mixture of isomeric compounds (with alpha and beta isomers) and inorganic salt impurities (typically phosphate and chloride). If a purchaser seeks the pure beta isomer, they are forced to separate the isomers, which is highly labor intensive, due to the need for repeat purifications. The repeated purifications can result in the loss of up to 50% of the product. Furthermore, removal of inorganic impurities, especially phosphate, is equally difficult. Purification of the product to achieve a high purity BGP is typically achieved by repeat crystallizations, resulting in further loss of product, and ultimately higher cost to the purchaser. In light of the current limitations, there is a need for a high-yield method for the synthesis of BGP of high purity.

SUMMARY OF THE INVENTION

The present invention provides a method of production for highly pure beta glycerol phosphate from the corresponding glycerol or protected glycerol compounds.

In one aspect the present invention encompasses a process for the preparation of a compound comprising Formula (VI). The process comprises (a) contacting a compound comprising Formula (I) with a protecting agent comprising $R^P$ to form a compound comprising Formula (II); (b) contacting the compound comprising Formula (II) with a phosphorylating agent comprising Z in the presence of a proton acceptor to form a compound comprising Formula (III); (c) contacting the compound comprising Formula (III) with water to form a compound comprising Formula (IV) and HZ; (d) contacting the compound comprising Formula (IV) with a proton acceptor comprising at least one metal ion (M) to form a compound comprising Formula (V); and (e) deprotecting the compound comprising Formula (V) to form the compound comprising Formula (VI) according to the following reaction scheme:

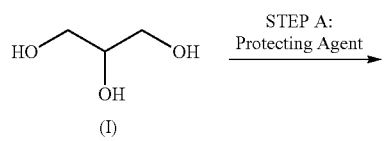

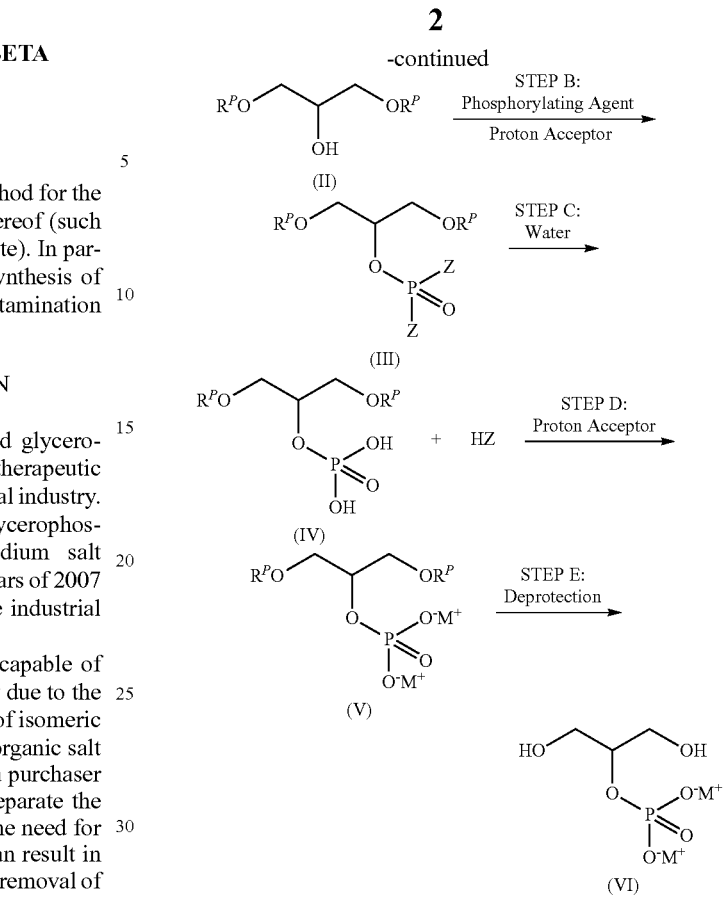

wherein:
$R^P$ is a protecting group;
Z is halogen; and
M is selected from the group consisting of Group IA, Group IIA, and transition metal ions.

Yet another aspect of the present invention comprises a process for the preparation of a compound comprising Formula (VI). The process comprises (a) contacting a compound comprising Formula (II) with a phosphorylating agent comprising Z in the presence of a proton acceptor to form a compound comprising Formula (III); (b) contacting the compound comprising Formula (III) with water to form a compound comprising Formula (IV) and HZ; (c) contacting the compound comprising Formula (IV) with a proton acceptor comprising at least one metal ion (M) to form a compound comprising Formula (V); and (d) deprotecting the compound comprising Formula (V) to form the compound comprising Formula (VI) according to the following reaction scheme:

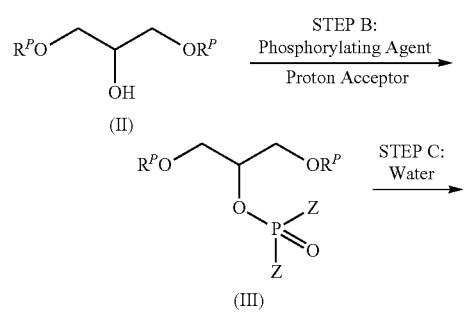

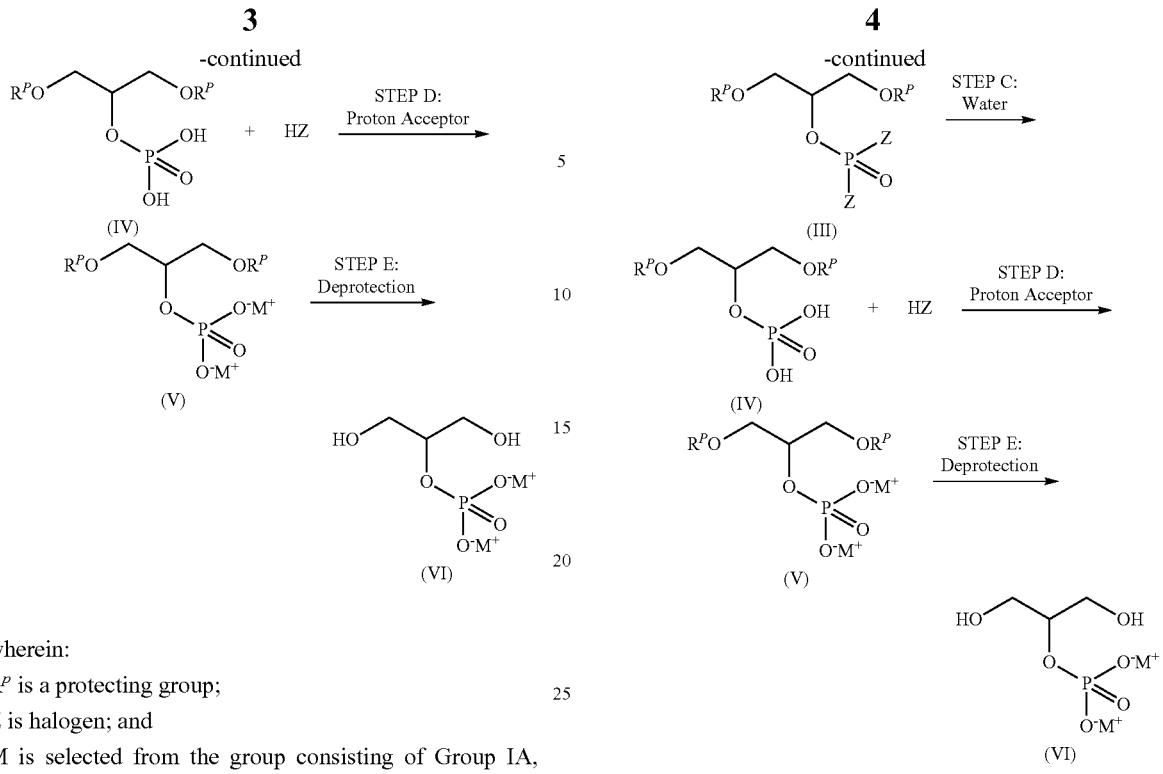

wherein:

R$^P$ is a protecting group;

Z is halogen; and

M is selected from the group consisting of Group IA, Group IIA, and transition metal ions.

Other aspects and features of the invention are detailed below.

DETAILED DESCRIPTION OF THE INVENTION

The present invention provides an efficient process for the production of beta glycerol phosphate and salts thereof of high purity. The beta glycerol phosphate and salts thereof (such as, e.g., glycerol 2-phosphate disodium salt hydrate) product generally comprises greater than about 99% by weight of the β-isomer of the compound. The process also prevents the formation of impurities and/or efficiently removes impurities during the course of the process.

(I) Synthesis of Beta Glycerol Phosphate from Glycerol

One aspect of the present invention provides a method for the synthesis of beta glycerol phosphate or salts thereof [i.e., a compound comprising Formula (VI)] using glycerol as the starting material. For purposes of illustration, Reaction Scheme 1 depicts the production of the compound comprising Formula (VI) from a compound comprising Formula (I) in accordance with this aspect of the invention:

Reaction Scheme 1:

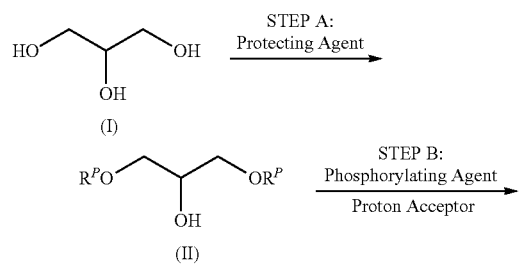

wherein:

R$^P$ is a protecting group;

Z is halogen; and

M is selected from the group consisting of Group IA, Group IIA, and transition metal ions.

(a) Step A: Conversion of Compound (I) to Compound (II)

Generally, the substrate for preparation of compound (II) corresponds to compound (I) depicted in Reaction Scheme 1. Step A comprises contacting the compound comprising Formula (I) with a protecting agent comprising R$^P$ to form the compound comprising Formula (II) according to Reaction Scheme 1. The compound comprising Formula (II) comprises a protecting group (R$^P$) at the alpha and gamma positions of the molecule.

The term "protecting group" as used herein denotes a group capable of protecting an oxygen atom, wherein the protecting group, subsequent to the reaction for which protection is employed, may be removed without disturbing the remainder of the molecule. Non-limiting examples of suitable protecting groups include acyls (e.g., pivaloyl (i.e., 2,2-dimethyl propanoyl), adamantanoyl, methanoyl, ethanoyl (i.e., acetyl), propanoyl, butanoyl, pentanoyl, and the like); benzyls and substituted benzyls (e.g., benzyloxy, mesitoyl, and so forth); ethers (e.g., allyl, triphenylmethyl (trityl or Tr), p-methoxybenzyl (PMB), p-methoxyphenyl (PMP), and the like); acetals (e.g., methoxymethyl (MOM), β methoxyethoxymethyl (MEM), tetrahydropyranyl (THP), ethoxy ethyl (EE), methylthiomethyl (MTM), 2 methoxy-2-propyl (MOP), 2 trimethylsilylethoxymethyl (SEM) and so forth); esters (e.g., benzoate (Bz), allyl carbonate, 2,2,2-trichloroethyl carbonate (Troc), 2-trimethylsilylethyl carbonate, and the like); silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and so forth). A variety of protecting groups and the synthesis thereof may be found in "Protective Groups in Organic Synthesis" by T. W. Greene and P. G. M. Wuts, John Wiley & Sons, 1999. Preferred protecting groups include acyl, benzyl, and substituted benzyl. In preferred embodiments, the protecting group may be pivaloyl, benzyl, benzyloxy, adamantanoyl, mesitoyl, and acetyl. In an exemplary embodiment, the protecting group may be pivaloyl.

The mole-to-mole ratio of the compound comprising Formula (I) to the protecting agent can and will vary. In general the mole-to-mole ratio of the compound comprising Formula (I) to the protecting agent may range from about 1:0.1 to about 1:10, or more preferably from about 1:1 to about 1:5. In exemplary embodiments, the mole-to-mole ratio of the compound comprising Formula (I) to the protecting agent may range from about 1:2 to about 1:3.

In general the reaction of Step A may be conducted at a temperature that ranges from about −30° C. to about 30° C. for a period of time that is sufficient to convert a substantial portion of the compound comprising Formula (I) to the compound comprising Formula (II). In one embodiment, the temperature may range from about −20° C. to about 10° C. In a preferred embodiment, the temperature may range from about −10° C. to about 5° C.

In addition, Step A is generally conducted in the presence of an organic solvent. Suitable organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, diethylene glycol, fluorobenzene, heptane, hexane, isobutylmethylketone, isopropyl acetate, methylethylketone, methyltetrahydrofuran, pentyl acetate, n-propyl acetate, tetrahydrofuran, toluene, and combinations thereof. In a preferred embodiment, the organic solvent is t-butyl methylether.

Step A may also be conducted in the presence of a proton acceptor. In general, the proton acceptor has a pKa of between about 7 and about 13, preferably between about 8 and about 10. Representative proton acceptors that may be employed include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic bases (such as, for example, pyridine, triethylamine, diisopropylethylamine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl) piperazine-1-ethanesulfonic acid (HEPES), 2-(4-morpholinyl) ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. In a preferred embodiment, the proton acceptor is pyridine.

Optionally, as detailed in the examples, the reaction mixture formed by the reaction of Step A may be quenched by the addition of the appropriate agents to remove the unreacted protecting agent and/or proton acceptor.

Additionally, the production of highly pure BGP is dependent upon minimizing the amount of the alpha isomer of the diprotected compound. This is accomplished by ensuring the compound comprising Formula (II) is predominantly composed of the beta isomer (i.e., 1,3-diprotected compound), rather than the alpha isomer (i.e., 1,2-diprotected compound). In general, high levels of the beta isomer help prevent the formation of impurities downstream and lessen the need to perform additional purifications leading to increased costs and decreased efficiency. Generally, the alpha isomer of the diprotected compound comprises less than about 20% by weight of compound comprising Formula (II). In another embodiment, the alpha isomer of the diprotected compound comprises less than about 15% by weight of the compound comprising Formula (II). In still another embodiment, the alpha isomer of the diprotected compound comprises less than about 10% by weight of the compound comprising Formula (II). In a preferred embodiment, the alpha isomer of the diprotected compound comprises less than about 5% by weight of the compound comprising Formula (II). In an exemplary embodiment, the alpha isomer of the diprotected compound comprises less than about 4%, 3%, 2%, or 1% by weight of the compound comprising Formula (II). In general, ensuring that the reaction never exceeds 0° C. helps to prevent isomerization.

(b) Step B: Conversion of Compound (II) to Compound (III)

Generally, the substrate for preparation of compound (III) corresponds to compound (II) depicted in Reaction Scheme 1. Step B of the invention comprises contacting a compound comprising Formula (II) with a phosphorylating agent comprising a halogen moiety (Z) in the presence of a proton acceptor to form a compound comprising Formula (III).

Phosphorylating agents result in the addition of a phosphate or substituted phosphoryl group to an organic compound. Generally, the phosphorylating agent is a compound comprising a formula selected from the group consisting of $O=P(Z)(X)_2$ and $P(Z)_n$, wherein O is oxygen; P is phosphorus; Z is halogen; X is independently selected from the group consisting of Z and {—}OR; and the variable n is an integer ranging from three to five. Furthermore, {—}OR comprises an oxygen (O) bound to a hydrocarbyl or substituted hydrocarbyl group (R). Preferably, R is a lower alkyl or substituted alkyl group; a lower alkenyl or substituted alkenyl group; or an aryl or substituted aryl group. In embodiments in which the phosphorylating agent comprises $P(Z)_n$, the reaction further comprises an oxidation step. Those of skill in the art are familiar with suitable oxidizing agents.

Non-limiting examples of suitable phosphorylating agents include phosphorus oxychloride ($POCl_3$), phosphorus oxyflouride ($POF_3$), phosphorus oxybromide ($POBr_3$), phosphorus oxyiodide ($POI_3$), dimethyl chlorophosphate ($POCl(OCH_3)_2$), diethyl chlorophosphate ($POCl(OCH_2CH_3)_2$), dipropyl chlorophosphate ($POCl(OCH_2CH_2CH_3)_2$), dibutyl chlorophosphate ($POCl(O(CH_2)_3CH_3)_2$), dipentyl chlorophosphate ($POCl(O(CH_2)_4CH_3)_2$), dihexyl chlorophosphate ($POCl(O(CH_2)_5CH_3)_2$), diheptyl chlorophosphate ($POCl(O(CH_2)_6CH_3)_2$), phosphorus trichloride ($PCl_3$), phosphorus tribromide ($PBr_3$) phosphorus triiodide ($PI_3$), phosphorus triflouride ($PF_3$), phosphorus pentachloride ($PCl_5$), phosphorus pentaflouride ($PF_5$), phosphorus pentabromide ($PBr_5$), and phosphorus pentaiodide ($PI_5$). In a preferred embodiment, the phosphorylating agent is phosphorus oxychloride.

Step B is generally conducted in the presence of a proton acceptor. In general, the proton acceptor has a pKa of between about 7 and about 13, preferably between about 8 and about 10. Representative proton acceptors that may be employed include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), alkyl amine bases (such as, for example, triethylamine, trimethylamine, tributylamine, diethylamine, and diisopropylethylamine), organic bases (such as, for example, pyridine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl)piperazine-1-ethanesulfonic acid (HEPES), 2-(4-morpholinyl)ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. In a preferred embodiment, the proton acceptor may be triethylamine, trimethylamine, tributylamine, or pyridine.

Step B generally proceeds in the presence of an organic solvent. In some embodiments, the organic solvent may be carried over from Step A of the reaction. Suitable organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, diethylene glycol, fluorobenzene, heptane, hexane, isobutylmethylketone, isopropyl acetate, methylethylketone, methyltetrahydrofuran, pentyl acetate, n-propyl acetate, tetrahydrofuran, toluene, and combinations thereof. In a preferred embodiment, the organic solvent may be t-butyl methylether.

The mole-to-mole ratio of the compound comprising Formula (II) to the phosphorylating agent can and will vary. In general, the mole-to-mole ratio of compound comprising Formula (II) to phosphorylating agent may be from about 1:0.1 to about 1:10. In another embodiment, the mole-to-mole ratio of compound comprising Formula (II) to phosphorylating agent may be from about 1:0.5 to about 1:5. In still another embodiment, the mole-to-mole ratio of compound comprising Formula (II) to phosphorylating agent may be from about 1:0.8 to about 1:2. In an exemplary embodiment, the mole-to-mole ratio of compound comprising Formula (II) to phosphorylating agent may be from about 1:1 to about 1:1.1.

In general the reaction of Step B may be conducted at a temperature that ranges from about −30° C. to about 30° C. for a period of time that is sufficient to convert a substantial portion of the compound comprising Formula (II) to the compound comprising Formula (III). In one embodiment, the temperature may range from about −20° C. to about 10° C. In a preferred embodiment, the temperature may range from about −10° C. to about 5° C. In general, ensuring that the reaction does not exceed 0° C. minimizes the formation of by-products.

The temperature range provided above is generally maintained for a sufficient period of time for the reagents to react. After the initial agitation, Step B may further comprise a warming phase for the remainder of the reaction, prior to initiating Step C. Generally, the reaction is warmed to a temperature that may range from about 5° C. to about 35° C. In a preferred embodiment, the temperature may range from about 15° C. to about 30° C.

(c) Step C: Conversion of Compound (III) to Compound (IV)

Generally, the substrate for preparation of compound (IV) corresponds to compound (III) depicted in Reaction Scheme 1. Step C of the invention comprises contacting a compound comprising Formula (III) with water to form a compound comprising Formula (IV).

The water added to the solution comprising the compound comprising Formula (III) is generally considered to be at least in the range of about 10% to about 80% by weight of the entire reaction mixture. In a preferred embodiment, the water present in the reaction mixture may range from at least about 20% to about 40%. However, excess amounts of water may be used for an efficient and safe quenching of the reaction mixture and to ensure efficient removal of impurities. The temperature of the reaction of Step C may range from about 5° C. to about 35° C. In a preferred embodiment, the temperature may range from about 20° C. to about 35° C. As in previous steps, ensuring that the reaction mixture does not exceed a certain temperature (e.g., about 35° C. in this step) helps prevent the formation of impurities.

Additionally, Step C typically further comprises a first partitioning step wherein the addition of the water leads to formation of an organic phase and an aqueous phase. The organic phase comprises the compound comprising Formula (IV) and the aqueous phase comprises impurities such as HZ. The first partitioning step comprises removing impurities from the reaction mixture via removal of the aqueous layer of the mixture. One of the primary impurities separated into the aqueous layer is HZ, as illustrated in Reaction Scheme 1. As described above, HZ comprises a hydrogen bonded to a halogen or a group comprising the formula {—}OR. The compound comprising HZ may include, but is not limited to hydrogen chloride, hydrogen fluoride, hydrogen bromide, hydrogen iodide, methanol, ethanol, propanol, or any alcohol formed by the bonding of hydrogen to the {—}OR group. In a preferred embodiment, in which the phosphorylating agent is phosphorus oxychloride ($POCl_3$), HZ is hydrogen chloride. The aqueous layer is subsequently separated using a technique known to those of skill in the art. The first partitioning step may be repeated by adding additional water and removing the aqueous phase until the reaction mixture has a pH of greater than about 4, and more preferably greater than about 5. In a preferred embodiment, after removal of the aqueous layer, the organic layer comprising the compound comprising Formula (IV) has a pH of greater than about 5.

Step C may further comprise a second partitioning step of the reaction mixture into two immiscible organic phases by adding a non-polar hydrocarbon solvent and a polar hydrocarbon solvent that is miscible in water. The partitioning separates the reaction mixture into a polar hydrocarbon solvent phase comprising the compound comprising Formula (IV) and a non-polar hydrocarbon solvent phase comprising at least one organic side product of the reaction process. The non-polar hydrocarbon solvent phase may comprise organic impurities present in the reaction mixture from Step A, such as, for example, a triple protected glycerol. The non-polar hydrocarbon may include, but is not limited to alkane and substituted alkane solvents (including cycloalkanes), aromatic hydrocarbons, esters, ethers, ketones, combinations thereof, and the like. Specific non-polar hydrocarbon solvents that may be employed, include, for example, benzene, butyl acetate, t-butyl methylether, t-butyl methylketone, chlorobenzene, chloroform, chloromethane, cyclohexane, dichloromethane, dichloroethane, diethyl ether, ethyl acetate, diethylene glycol, fluorobenzene, heptane, hexane, isobutylmethylketone, isopropyl acetate, methylethylketone, methyltetrahydrofuran, pentyl acetate, n-propyl acetate, tetrahydrofuran, toluene, and combinations thereof. In a preferred embodiment, the non-polar hydrocarbon solvent may be heptane, hexane, pentane, octane, or cyclopentane. In an exemplary embodiment, the non-polar hydrocarbon is heptane.

The polar hydrocarbon solvent that is miscible in water may comprise either a polar aprotic solvent or a polar protic solvent. Non-limiting examples of suitable aprotic solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), 1,4-dioxane, N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), 2-methyl tetrahydrofuran, toluene, trichloromethane, and combinations thereof. Furthermore, suitable examples of protic solvents include, but are not limited to, methanol, ethanol, isopropanol, n-propanol, isobutanol, n-butanol, s-butanol, t-butanol, formic acid, acetic acid, water, and combinations thereof. In a preferred embodiment, the polar hydrocarbon solvent may be ethanol, methanol, propanol, or acetonitrile. In an exemplary embodiment, the polar hydrocarbon solvent is methanol.

The polar hydrocarbon solvent that is miscible in water is typically combined with water to create a solvent comprising a concentration of water in polar hydrocarbon solvent of about 1% to about 25%. In a preferred embodiment, the concentration of water in polar hydrocarbon solvent may range from about 5% to about 15%.

The removal of impurities is an important step in the process of the invention because impurities such as HZ or other side products not only affect the purity of the final product, but they may react with reagents in Steps D and E, further decreasing the purity and efficiency of the process. For these reasons, the concentration of side products in the reaction mixture prior to initiation of Step D are preferably less than about 10%. In a preferred embodiment, the concentration of side products in the reaction mixture prior to initiation of Step D may be less than about 5%.

(d) Step D: Conversion from Compound (IV) to Compound (V)

Generally, the substrate for preparation of compound (V) corresponds to compound (IV) depicted in Reaction Scheme 1. Step D of the invention comprises contacting a compound comprising Formula (IV) with a proton acceptor comprising at least one metal ion (M) to form a compound comprising Formula (V).

The metal ion (M) may be a Group IA metal ion, a Group IIA metal ion, or a transition metal ion. Non-limiting examples of preferred metal ions include sodium, potassium, lithium, calcium, magnesium, calcium, iron, manganese, copper, and zinc. In an exemplary embodiment, the metal ion is sodium.

Generally, the proton acceptor comprising at least one metal ion has a pKa of between about 7 and about 13, preferably between about 8 and about 10. Representative proton acceptors that may be employed include, but are not limited to, metal borates (such as, for example, $Na_3BO_3$), metal di- and tri-basic phosphates (such as, for example, $Na_2HPO_4$ and $Na_3PO_4$), metal bicarbonates (such as, for example, $NaHCO_3$, $KHCO_3$, mixtures thereof, and the like), metal hydroxides (such as, for example, NaOH, KOH, CaOH, $Fe(OH)_2$, $Cu(OH)_2$, $Zn(OH)_2$, mixtures thereof, and the like), metal carbonates (such as, for example, $Na_2CO_3$, $K_2CO_3$, $Li_2CO_3$, $CaCO_3$, $MnCO_3$, $FeCO_3$, $CuCO_3$, $ZnCO_3$, mixtures thereof, and the like), or combinations thereof. In a preferred embodiment, the proton acceptor may be a metal borate, a metal carbonate, a metal bicarbonate, or a metal hydroxide. In another preferred embodiment, the proton acceptor may be a metal hydroxide. In an exemplary embodiment, the proton acceptor may be sodium hydroxide.

The amount of proton acceptor added to the reaction mixture of Step D can and will vary. In general, the proton acceptor is added to the reaction mixture to raise the pH of the reaction mixture. Generally, the pH of the reaction mixture in Step D may be greater than about 9. In a preferred embodiment, the pH of the reaction mixture in Step D may be greater than about 11. In an exemplary embodiment, the pH of the reaction mixture may range from about 11 to about 12. In preferred embodiments, the concentration of the proton acceptor generally may range from about 20% to about 80% (w/v). In a preferred embodiment, the concentration of the proton acceptor may range from about 40% to about 60% (w/v).

Step D additionally typically comprises raising the temperature of the reaction mixture from about 40° C. to about 100° C. In a preferred embodiment, the temperature of the reaction mixture in Step D may range from about 60° C. to about 80° C.

(e) Step E: Conversion from Compound (V) to Compound (VI)

Generally, the substrate for preparation of compound (VI) corresponds to compound (V) depicted in Reaction Scheme 1. Step E of the invention comprises deprotecting the compound comprising Formula (V) to form a compound comprising Formula (VI). Deprotection generally refers to the dissociation of protecting groups from the diprotected compound comprising Formula (V). The deprotection reaction may include any chemical process capable of dissociating the protecting groups from the compound comprising Formula (V), and one skilled in the art will appreciate that many possible reaction types exist, depending upon the protecting group chosen in Step A. In a preferred embodiment, the deprotection reactions include hydrolysis or hydrogenolysis of the protecting groups.

Upon completion of the reaction, the reaction mixture may be cooled to a temperature ranging from about −20° C. to about 40° C. to facilitate isolation of the product. In a preferred embodiment, the temperature may range from about −10° C. to about 10° C. Once the reaction mixture has cooled, filtration may be performed (for example by use of a 1-3 micron polypad) to remove impurities. Those of skill in the art will appreciate that other methods may be used to isolate the compound comprising Formula (VI). The final product may be washed and dried, and analyzed by suitable methods known to those of skill in the art.

The yield of the compound comprising Formula (VI) may vary. Typically, the yield of the compound may be at least about 30%. In a preferred embodiment, the yield of the compound may be at least about 40%.

Additionally, the beta isomer of the compound comprising Formula (VI) comprises greater than about 85% by weight of the compound comprising Formula (VI). In another embodiment, the beta isomer of the compound comprising Formula (VI) comprises greater than about 95% by weight of the compound comprising Formula (VI). In a preferred embodiment, the beta isomer of the compound comprising Formula (VI) comprises greater than about 99% by weight of the compound comprising Formula (VI). In another preferred embodiment, the beta isomer of the compound comprising Formula (VI) comprises greater than about 99.9% by weight of the compound comprising Formula (VI).

Conversely, the alpha isomer of the compound comprising Formula (VI) comprises less than about 15% by weight of the compound comprising Formula (VI). In another embodiment, the alpha isomer of the compound comprising Formula (VI) comprises less than about 5% by weight of the compound comprising Formula (VI). In still another embodiment, the alpha isomer of the compound comprising Formula (VI) comprises less than about 1% by weight of the compound comprising Formula (VI). In a preferred embodiment, the alpha isomer of the compound comprising Formula (VI) comprises less than about 0.1% by weight of the compound comprising Formula (VI).

(II) Synthesis of Beta Glycerol Phosphate from 1,3-Diprotected Glycerol

Another aspect of the present invention encompasses a method for the synthesis of a compound comprising Formula (VI) using 1,3-diprotected glycerol as the starting material. That is, Step A, as depicted in Reaction Scheme 1, is optional. Therefore, the diprotected compound comprising Formula (II) is provided as starting material. Examples of suitable protecting groups are detailed above in (I)(a). In some embodiments, commercially available diacetin (i.e., glycerol diacetate), 1,3-dibenzyl glycerol, or 1,3-dibenzyloxy glycerol (i.e., 1,3-dibenzyloxy-2-propanol) may be used as starting material. The alternate process, therefore, commences with Step B as detailed above.

DEFINITIONS

To facilitate understanding of the invention, several terms are defined below:

The term "acyl," as used herein alone or as part of another group, denotes the moiety formed by removal of the hydroxy group from the group COOH of an organic carboxylic acid, e.g., RC(O), wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorus, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Lab-Scale Production of Beta Glycerol Phosphate

Beta glycerol phosphate was prepared according to the following reaction scheme, wherein $R^P$ is a protecting group:

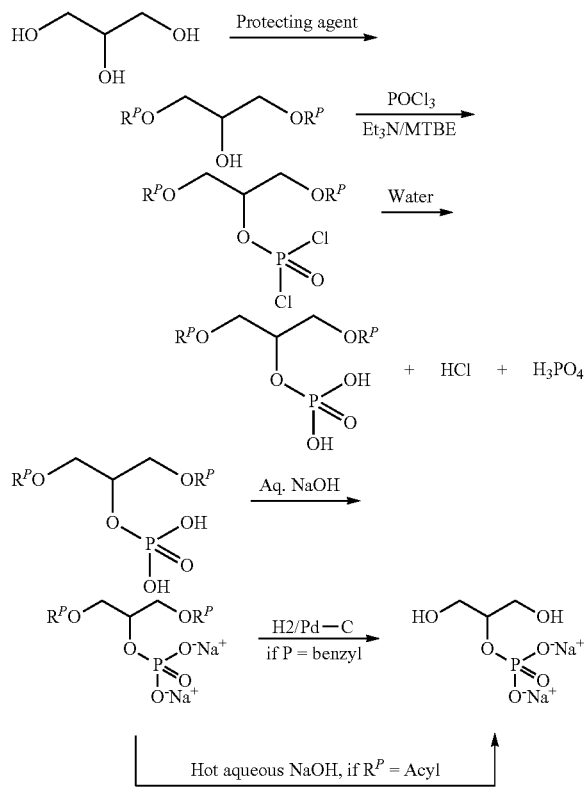

The following example was designed as a qualification run within the lab, to test the reaction. One kg of glycerol in pyridine and tert-butyl methyl ether (tBME) was reacted with 2.4 kg of 2,2-dimethylpropanoyl chloride at temperatures which ranged from (−5)° C. to 0° C., but never exceeding 0° C. After the reaction was complete, as verified by gas chromatography (GC), the slurry was quenched by addition of 6N hydrochloric acid (HCl). The slurry was subsequently washed two additional times with 6N HCl to ensure that excess pyridine was removed. The slurry was then tested by GC to verify that less than 1% of the original pyridine remained. In the next step, the tBME solvent layer was washed with water, then 1N sodium bicarbonate, and finally once more with water. The organic layer was subsequently azeotropically distilled to less than 0.2% water content. The process of distillation took three charges of tBME to achieve this result.

Next, 0.7 kg of triethylamine was added to the cooled (−5° C.) tBME solution obtained by the prior process. Then, 0.84 kg of phosphoryl chloride (also termed phosphorus oxychloride) was added to the solution. The temperature fluctuated between (−5° C. and 0° C., but never exceeded 0° C. After the slurry was agitated for two hours at the cooled temperature between (−5° C. and 0° C., it was allowed to warm to 25° C. for the completion of the reaction, which took approximately 12 hours, and was verified by thin layer chromatography (TLC).

In the next step, the slurry was quenched with 5 kg of water, while maintaining the temperature in the range of 30° C. to 35° C., ensuring that the slurry did not exceed 35° C. The slurry was subsequently washed with an additional 5 kg of water before proceeding. Next, the solvent (primarily tBME) was exchanged for heptane by means of distillation. After an additional two charges of heptane, the concentration of tBME was less than 1%, as verified by GC. Subsequently, the product of interest (1,3-dipivaloyl glyceryl phosphoric acid) was removed from the heptane layer by adding 3 L of 5% water in methanol. The methanol layer containing the product was then extracted by additional exposure to two 5 kg of heptane, to ensure that the product was not contaminated by tripivalate impurities. The tripivalate impurity level was less than 5% as verified by TLC and hydrogen nuclear magnetic resonance (H NMR).

Upon verification that the tripivalate concentration was less than 5%, the aqueous methanol solution was treated with 50% sodium hydroxide, to raise the pH to a level between 12 and 13. After the pH had stabilized for approximately thirty minutes, the temperature of the slurry was raised to 65° C., while maintaining the pH level between 12 and 13. Additional amounts of 50% sodium hydroxide were added to the slurry to remove the protecting acyl groups from positions 1 and 3. The reaction was monitored by H NMR until the reaction was considered complete.

Upon verification of completion by H NMR, the slurry was cooled to 0° C., and was suction filtered through a 1-3 micron polypad. Filtration was subsequently performed at 2° C. to 5° C. to improve filtration rate. The filtrate was dried and analyzed, yielding 1.5 kg of crude product. The crude product was slurried in 4.75 kg of methanol and 0.25 L water (5% water in methanol) at room temperature for one hour. Finally, the slurried product was again suction filtered through a 1-3 micron polypad, dried, and analyzed to produce 1.45 kg of product.

Thus, one kg of glycerol was reacted according to the process described above to produce 1.45 kg of highly pure, commercially desirable beta glycerol phosphate (glycerol 2-phosphate disodium salt hydrate).

Example 2

Larger Scale Production of Beta Glycerol Phosphate

The following example was performed to test the efficiency of the process at a large scale. First, 12.7 kg of glycerol in pyridine and tBME was reacted with 38.1 kg of 2,2-dimethylpropanoyl chloride (pivaloyl chloride). The reaction was conducted, maintaining the temperature in the range of (−5)° C. to 0° C., ensuring that the temperature did not rise above 0° C. After the reaction was complete, as verified by GC, the slurry was quenched with 6N HCl, and subsequently washed an additional three times with 6N HCl to remove excess pyridine. Once the concentration of pyridine was less than 1%, as verified by GC, the remaining tBME solvent layer was washed with water and 1N sodium bicarbonate. The water layer was azeotropically distilled by means of three charges of tBME to a concentration of less than 0.2%.

In the next step, 12.9 kg of TEA was added to the cooled ((−5)° C.) tBME solution obtained by the prior process. Subsequently, 18.45 kg of phosphoryl chloride was slowly added to the slurry, ensuring that the temperature was maintained in the range from (−5)° C. to 0° C. After the slurry was agitated for two hours, it was warmed to 25° C., for the remainder of the reaction (approximately 13 hours), as verified by TLC.

After completion, the slurry was then quenched with 42 kg of water at a temperature range of 30° C. to 35° C. The reaction slurry was subsequently quenched onto 30-45 kg of water for three additional cycles. In the next step, the tBME was exchanged to heptane by means of distillation. After the initial distillation, and two further charges of heptane, a residual tBME concentration of less than 1% was achieved. The product was then extracted from the heptane layer using 54 L of 5% water in methanol. The aqueous methanol layer comprising product and tripivalate impurities was extracted two additional times using heptane, each extraction cycle consisting of approximately 26-28 kg heptane, to further eliminate tripivalate impurities. Upon verification by TLC that tripivalate impurities were less than 5%, the solution was filtered to remove haziness within the solution.

Next, the aqueous methanol layer comprising product and less than 5% tripivalate impurities was treated with 50% sodium hydroxide, until the pH raised to a level between 12 and 13. The slurry was then heated to 65° C., while maintaining pH in the range of 12 to 13. In the event that pH decreased below 12, additional 50% sodium hydroxide was used to restore solution to the desired pH range. The reaction was monitored by H NMR for reaction completion, and upon completion was cooled to 0° C.

Once the slurry reached 0° C., it was filtered by centrifuge, dried and analyzed. A total of 28.9 kg of crude product was isolated, and was subsequently slurried with 58 kg of methanol and 8 L of water at room temperature for approximately 5 hours. The treated product was filtered through a Nutsche pressure filter, dried, and analyzed, to produce 20.6 kg of product.

Thus, 12.7 kg of glycerol was reacted according to the process described above, and yielded 20.6 kg of beta glycerol phosphate (glycerol 2-phosphate disodium salt hydrate).

What is claimed is:
1. A process for the preparation of a compound of Formula (VI),

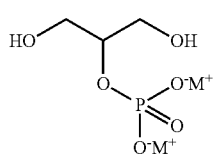

the process comprising:
(a) contacting a compound of Formula (I)

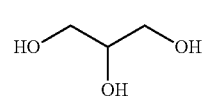

with a protecting agent comprising $R^p$ to form a compound of Formula (II)

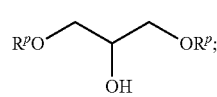

(b) contacting the compound of Formula (II) with a phosphorylating agent comprising Z in the presence of a proton acceptor to form a compound of Formula (III)

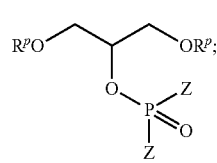

(c) contacting the compound of Formula (III) with water to form HZ and a compound of Formula (IV)

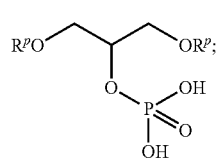

(d) contacting the compound of Formula (IV) with a proton acceptor comprising at least one metal ion (M) to form a compound of Formula (V)

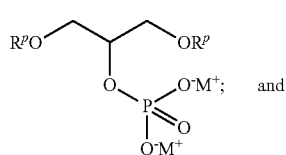

(e) deprotecting the compound of Formula (V) to form the compound of Formula (VI);
wherein:
$R^p$ is a protecting group;
Z is halogen; and
M is selected from the group consisting of Group IA, Group IIA, and transition metal ions.
2. The process of claim 1, wherein $R^p$ is selected from the group consisting of acyl, benzyl, and substituted benzyl.
3. The process of claim 1, wherein the mole-to-mole ratio of the compound of Formula (I) to the protecting agent is about 1:2 to about 1:3, and the reaction of step (a) is performed at a temperature from about −10° C. to about 5° C. and in the presence of an organic solvent.

4. The process of claim 1, wherein the amount of α-isomer of the compound of Formula (II) is less than about 5% by weight of the amount of the compound of Formula (II).

5. The process of claim 1, wherein the phosphorylating agent is selected from the group consisting of $O=P(Z)(X)_2$ and $P(Z)_n$, wherein Z is halogen; X is independently selected from the group consisting of Z and {—}OR; R is selected from the group consisting of hydrocarbyl or substituted hydrocarbyl; and the variable n is an integer from three to five.

6. The process of claim 1, wherein the phosphorylating agent is phosphorus oxychloride; and the proton acceptor of step (b) is selected from the group consisting of an alkyl amine base, a substituted pyridine, and an inorganic base.

7. The process of claim 1, wherein the mole-to-mole ratio of the compound of Formula (II) to the phosphorylating agent is from about 1:1 to about 1:1.1 and the reaction of step (b) is performed at a temperature that does not exceed about 0° C.

8. The process of claim 1, wherein the reaction mixture of step (b) is heated to a temperature from about 15° C. to about 30° C. after the reaction is completed and prior to the addition of water in step (c).

9. The process of claim 8, wherein the amount of water in the reaction mixture of step (c) comprises at least about 20% by weight and the reaction is performed at a temperature from about 20° C. to about 35° C.

10. The process of claim 9, wherein the addition of water leads to the formation of an organic phase and an aqueous phase such that a first partitioning step is conducted, the organic phase comprising the compound of Formula (IV) and the aqueous phase comprising HZ, followed by removal of the aqueous phase from the reaction mixture.

11. The process of claim 10, wherein the first partitioning step and the removal of the aqueous phase is repeated until the reaction mixture has a pH of greater than about 5.

12. The process of claim 11, further comprising a second partitioning step of the reaction mixture of step (c) into two immiscible organic phases by adding a non polar hydrocarbon solvent and a polar hydrocarbon solvent that is miscible in water, the compound of Formula (IV) being present in the polar hydrocarbon solvent and at least one organic side product being present in the non polar hydrocarbon solvent, followed by removal of the non polar hydrocarbon solvent phase from the reaction mixture.

13. The process of claim 12, wherein the organic side product comprises a triple protected glycerol.

14. The process of claim 12, wherein the non polar hydrocarbon solvent is selected from the group consisting of heptane, pentane, hexane, octane, and cyclopentane; and the polar hydrocarbon solvent is selected from the group consisting of methanol, ethanol, propanol, and acetonitrile.

15. The process of claim 1, wherein the proton acceptor of step (d) is selected from the group consisting of a metal hydroxide, metal bicarbonate, and metal carbonate.

16. The process of claim 1, wherein the proton acceptor of step (d) is added to the reaction mixture in an amount such that the pH of the reaction mixture is greater than about 11.

17. The process of claim 1, wherein the proton acceptor of step (d) comprises sodium hydroxide at a concentration of about 40% to about 60% and the reaction is performed at a temperature from about 60° C. to about 80° C.

18. The process of claim 1, wherein the deprotection reaction of step (e) comprises removal of the $R^p$ groups from the compound of Formula (V) by a method selected from the group consisting of hydrolysis and hydrogenolysis.

19. The process of claim 1, wherein the compound of Formula (VI) is isolated from the reaction mixture of step (e) by adding a solvent comprising from about 5% to about 15% water in alcohol followed by filtration of the reaction mixture.

20. The process of claim 1, wherein $R^p$ is selected from the group consisting of acyl, benzyl, and substituted benzyl, the mole-to-mole ratio of the compound of Formula (I) to the protecting agent is about 1:2 to about 1:3 and the reaction of step (a) is performed at a temperature from about −10° C. to about 5° C.; the proton acceptor of step (b) is selected from the group consisting of an alkyl amine base, a substituted pyridine, and an inorganic base; the mole-to-mole ratio of the compound of Formula (II) to phosphorylating agent is about 1:1 to about 1:1.1 and the reaction of step (b) is performed at a temperature that does not exceed about 0° C.; the reaction mixture of step (b) is heated to a temperature from about 15° C. to about 30° C. after the reaction is completed and prior to the addition of water in step (c); the amount of water in the reaction mixture of step (c) comprises at least about 20% by weight and the reaction is performed at a temperature from about 20° C. to about 35° C.; the proton acceptor of step (d) is added to the reaction mixture in an amount such that the pH of the reaction mixture is greater than about 11, and the reaction is conducted at a temperature of about 60° C. to about 80° C.; and step (e) comprises a method selected from the group consisting of hydrolysis and hydrogenolysis.

21. The process of claim 20, wherein the addition of water at step (c) leads to the formation of an organic phase and an aqueous phase such that a first partitioning step is conducted, the organic phase comprising the compound of Formula (IV) and the aqueous phase comprising HZ, followed by removal of the aqueous phase from the reaction mixture.

22. The process of claim 21, wherein the first partitioning step and the removal of the aqueous phase is repeated until the reaction mixture has a pH of greater than about 5.

23. The process of claim 22, further comprising a second partitioning step of the reaction mixture of step (c) into two immiscible organic phases by adding a non polar hydrocarbon solvent and a polar hydrocarbon solvent that is miscible in water, the compound of Formula (IV) being present in the polar hydrocarbon solvent and at least one organic side product being present in the non polar hydrocarbon solvent, followed by removal of the non polar hydrocarbon solvent phase from the reaction mixture.

24. The process of claim 23, wherein the organic side product comprises a triple protected glycerol.

25. The process of claim 23, wherein the non polar hydrocarbon solvent is selected from the group consisting of heptane, pentane, hexane, octane, and cyclopentane; and the polar hydrocarbon solvent is selected from the group consisting of methanol, ethanol, propanol, and acetonitrile.

26. The process of claim 25, wherein $R^p$ is selected from the group consisting of pivaloyl, benzyl, adamantanoyl, mesitoyl, and acetyl; the proton acceptor of step (b) is triethylamine; the phosphorylating agent is phosphorus oxychloride, Z is chloride, and the proton acceptor of step (d) is sodium hydroxide.

27. The process of claim 26, wherein the organic solvent added in step (a) is t-butyl methyl ether; the non polar hydrocarbon solvent of the second partitioning step of step (c) is heptane and the polar hydrocarbon solvent of the second partitioning step of step (c) is methanol.

28. The process of claim 27, wherein $R^p$ is selected from the group consisting of pivaloyl and benzyl.

29. The process of claim 1, wherein $R^p$ is selected from the group consisting of acyl, benzyl, and substituted benzyl; the proton acceptor of step (b) is triethylamine; the phosphorylating agent is phosphorus oxychloride, Z is chloride, and the proton acceptor of step (d) is sodium hydroxide.

30. The process of claim 29, wherein $R^p$ is selected from the group consisting of pivaloyl, benzyl, adamantanoyl, mesitoyl, and acetyl.

31. The process of claim 1, wherein the yield of the compound of Formula (VI) is at least about 40%.

32. The process of claim 1, wherein the amount of β-isomer of the compound of Formula (VI) is greater than about 99% by weight of the amount of the compound of Formula (VI).

33. The process of claim 1, wherein the amount of α-isomer of the compound of Formula (VI) is less than about 1% by weight of the amount of the compound of Formula (VI).

34. A process for the preparation of a compound of Formula (VI),

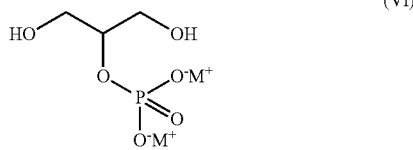

the process comprising:

(b) contacting a compound of Formula (II)

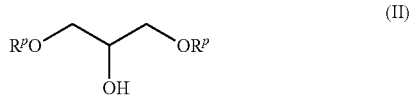

with a phosphorylating agent comprising Z in the presence of a proton acceptor to form a compound of Formula (III)

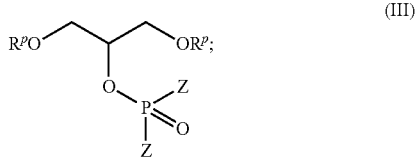

(c) contacting the compound of Formula (III) with water to form HZ and a compound of Formula (IV)

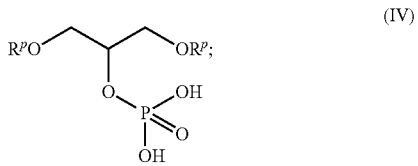

(d) contacting the compound of Formula (IV) with a proton acceptor comprising at least one metal ion (M) to form a compound of Formula (V)

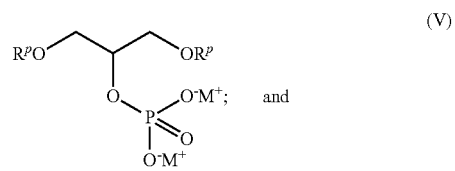

(e) deprotecting the compound of Formula (V) to form the compound of Formula (VI);

wherein:
$R^p$ is a protecting group;
Z is halogen; and
M is selected from the group consisting of Group IA, Group IIA, and transition metal ions.

35. The process of claim 34, wherein $R^p$ is selected from the group consisting of acyl, benzyl, and substituted benzyl.

36. The process of claim 34, wherein the phosphorylating agent is selected from the group consisting of $O{=}P(Z)(X)_2$ and $P(Z)_n$, wherein Z is halogen; X is independently selected from the group consisting of Z and {—}OR; R is selected from the group consisting of hydrocarbyl or substituted hydrocarbyl; and the variable n is an integer from three to five.

37. The process of claim 34, wherein the phosphorylating agent is phosphorus oxychloride, and the proton acceptor of step (b) is selected from the group consisting of an alkyl amine base, a substituted pyridine, and an inorganic base.

38. The process of claim 34, wherein the mole-to-mole ratio of the compound of Formula (II) to the phosphorylating agent is from about 1:1 to about 1:1.1, and the reaction of step (b) is performed at a temperature that does not exceed about 0° C. and in the presence of an organic solvent.

39. The process of claim 34, wherein the reaction mixture of step (b) is heated to a temperature from about 15° C. to about 30° C. after the reaction is completed and prior to the addition of water in step (c).

40. The process of claim 39, wherein the amount of water in the reaction mixture of step (c) comprises at least about 20% by weight and the reaction is performed at a temperature from about 20° C. to about 35° C.

41. The process of claim 40, wherein the addition of water leads to the formation of an organic phase and an aqueous phase such that a first partitioning step is conducted, the organic phase comprising the compound of Formula (IV) and the aqueous phase comprising HZ, followed by removal of the aqueous phase from the reaction mixture.

42. The process of claim 41, wherein the first partitioning step and the removal of the aqueous phase is repeated until the reaction mixture has a pH of greater than about 5.

43. The process of claim 42, further comprising a second partitioning step of the reaction mixture of step (c) into two immiscible organic phases by adding a non polar hydrocarbon solvent and a polar hydrocarbon solvent that is miscible in water, the compound of Formula (IV) being present in the polar hydrocarbon solvent and at least one organic side product being present in the non polar hydrocarbon solvent, followed by removal of the non polar hydrocarbon solvent phase from the reaction mixture.

44. The process of claim 43, wherein the organic side product comprises a triple protected glycerol.

45. The process of claim 43, wherein the non polar hydrocarbon solvent is selected from the group consisting of heptane, pentane, hexane, octane, and cyclopentane; and the polar hydrocarbon solvent is selected from the group consisting of methanol, ethanol, propanol, and acetonitrile.

46. The process of claim 34, wherein the proton acceptor of step (d) is selected from the group consisting of a metal hydroxide, metal bicarbonate, and metal carbonate.

47. The process of claim 34, wherein the proton acceptor of step (d) is added to the reaction mixture in an amount such that the pH of the reaction mixture is greater than about 11.

48. The process of claim 34, wherein the proton acceptor of step (d) comprises sodium hydroxide at a concentration of about 40% to about 60% and the reaction is conducted at a temperature from about 60° C. to about 80° C.

49. The process of claim 34, wherein the deprotection reaction of step (e) comprises removal of the $R^p$ groups from the compound of Formula (V) by a method selected from the group consisting of hydrolysis and hydrogenolysis.

50. The process of claim 34, wherein $R^p$ is selected from the group consisting of acyl, benzyl, and substituted benzyl; the proton acceptor of step (b) is selected from the group consisting of an alkyl amine base, a substituted pyridine, and an inorganic base, the mole-to-mole ratio of the compound of Formula (II) to phosphorylating agent is about 1:1 to about 1:1.1 and the reaction of step (b) is performed at a temperature that does not exceed about 0° C.; the reaction mixture of step (b) is heated to a temperature of about 15° C. to about 30° C. after the reaction is completed and prior to the addition of water in step (c); the amount of water in the reaction mixture of step (c) comprises at least about 20% by weight and the reaction is performed at a temperature from about 20° C. to about 35° C.; the proton acceptor of step (d) is added to the reaction mixture in an amount such that the pH of the reaction mixture is greater than about 11, and the reaction is conducted at a temperature of about 60° C. to about 80° C.; and step (e) comprises a method selected from the group consisting of hydrolysis and hydrogenolysis.

51. The process of claim 50, further comprising conducting a first partitioning step by adding an organic solvent to the reaction mixture of step (c) when the reaction is complete to form an organic phase and an aqueous phase, the organic phase comprising the compound of Formula (IV) and the aqueous phase comprising HZ, followed by removal of the aqueous phase from the reaction mixture.

52. The process of claim 51, wherein the first partitioning step and the removal of the aqueous phase is repeated until the reaction mixture has a pH of greater than about 5.

53. The process of claim 52, further comprising a second partitioning step of the reaction mixture of step (c) into two immiscible organic phases by adding a non polar hydrocarbon solvent and a polar hydrocarbon solvent that is miscible in water, the compound of Formula (IV) being present in the polar hydrocarbon solvent and at least one organic side product being present in the non polar hydrocarbon solvent, followed by removal of the non polar hydrocarbon solvent phase from the reaction mixture.

54. The process of claim 53, wherein the non polar hydrocarbon solvent is selected from the group consisting of heptane, pentane, hexane, octane, and cyclopentane; and the polar hydrocarbon solvent is selected from the group consisting of methanol, ethanol, propanol, and acetonitrile.

55. The process of claim 54, wherein $R^p$ is selected from the group consisting of pivaloyl, benzyl, adamantanoyl, mesitoyl, and acetyl; the proton acceptor of step (b) is triethylamine; the phosphorylating agent is phosphorus oxychloride, Z is chloride, and the proton acceptor of step (d) is sodium hydroxide.

56. The process of claim 55, wherein the organic solvent added in step (b) is t-butyl methyl ether; the non polar hydrocarbon solvent of the second partitioning step of step (c) is heptane and the polar hydrocarbon solvent of the second partitioning step of step (c) is methanol.

57. The process of claim 34, wherein $R^p$ is selected from the group consisting of acyl, benzyl, and substituted benzyl; the proton acceptor of step (b) is triethylamine; the phosphorylating agent is phosphorus oxychloride, Z is chloride, and the proton acceptor of step (d) is sodium hydroxide.

58. The process of claim 57, wherein $R^p$ is selected from the group consisting of pivaloyl, benzyl, adamantanoyl, mesitoyl, and acetyl.

59. The process of claim 34, wherein the yield of the compound of Formula (VI) is at least 40%.

60. The process of claim 34, wherein the amount of β-isomer of the compound of Formula (VI) is greater than about 99% by weight of the amount of the compound of Formula (VI).

61. The process of claim 34, wherein the amount of α-isomer of the compound of Formula (VI) is less than about 1% by weight of the amount of the compound of Formula (VI).

* * * * *